United States Patent [19]

Ohlrogge et al.

[11] Patent Number: 5,430,134
[45] Date of Patent: Jul. 4, 1995

[54] METHOD FOR PRODUCTION OF PETROSELINIC ACID AND OMEGA12 HEXADECANOIC ACID IN TRANSGENIC PLANTS

[75] Inventors: John B. Ohlrogge, Okemos; Edgar B. Cahoon, Lansing, both of Mich.; John Shanklin, Upton, N.Y.; Christopher R. Somerville, Okemos, Mich.

[73] Assignee: Michigan State University, East Lansing, Mich.

[21] Appl. No.: 926,788

[22] Filed: Aug. 7, 1992

[51] Int. Cl.⁶ ............................................. C12N 15/29
[52] U.S. Cl. ................................ 536/23.2; 530/377; 800/205; 800/250; 435/183
[58] Field of Search ............................. 536/23.6, 23.2; 800/205, 250, DIG. 43; 935/67; 530/377; 435/183

[56] References Cited

FOREIGN PATENT DOCUMENTS

94/01565  1/1994  WIPO .

OTHER PUBLICATIONS

Somerville, et al (Apr. 1991) Science 252:80-87.
Knauf (Feb. 1987) Tibtech 5:40-46.
Napoli, et al (Apr. 1990) The Plant Cell 2:279-289.
Thompson, et al (Mar. 1991) Proc. Natl. Acad. Sci, USA 88:2578-2582.
Knutzon, et al (1991) Plant Physiol 96:344-345.
Wada, et al (13 Sep. 1990) Nature 347:200-203.
Kleiman et al (1982) Journal of Am. Oil Chem. Soc. 59:29-38.

*Primary Examiner*—Che S. Chereskin
*Attorney, Agent, or Firm*—Foley and Lardner

[57] ABSTRACT

The present invention relates to a process for producing lipids containing the fatty acid petroselinic acid in plants. The production of petroselinic acid is accomplished by genetically transforming plants which do not normally accumulate petroselinic acid with a gene for a ω12 desaturase from another species which does normally accumulate petroselinic acid.

5 Claims, 14 Drawing Sheets

FIG. 3

```
  1   TCG GCA CGA GCT CCA ACA TTT CTC AAG GCC TCT ACT CTT GGC ATC CCC    48
  1    S   A   R   A   P   T   F   L   K   A   S   T   L   G   I   P    16

49   CCT TTG GAG GTT GAG AAT AAA AAG AAG CCT TTC ACT CCA AGA GAG         96
 17    P   L   E   V   E   N   K   K   K   P   F   T   P   R   E         32

97   GTA CAT GTT CAA GTG ACC CAC TCT ATG CCA CCA GAG AAG ATT GAG ATC   144
 33    V   H   V   Q   V   T   H   S   M   P   P   E   K   I   E   I    48

145   TTT AAA TCT TTA CAT AAA TGG GCT GAG CAG GAC CTG CTG GTA CAC TTA   192
 49    F   K   S   L   H   K   W   A   E   Q   D   L   L   V   H   L    64

193   AAG CCT GTT GAG AAA TGT TGG CAG TAT GTT GTT CTG CCA GAN AAG       240
 65    K   P   V   E   K   C   W   Q   Y   V   V   L   P   X   K        80

241   GAA ATT CCT GAT GAA TAT TAT GTT GTT TTA GTG GGC GAT ATG ATA ACA   288
 81    E   I   P   D   E   Y   Y   V   V   L   V   G   D   M   I   T    96

289   GAA GAA GCT CTT CCA ACT TAC CAG ACA ATG CTT AAC ACT CTT GAT GGT   336
 97    E   E   A   L   P   T   Y   Q   T   M   L   N   T   L   D   G   112

337   GAA CGA GAT GAA ACT GGT GCA AGC CTT TCC TGG GCT ATC TGG ACC       384
113    E   R   D   E   T   G   A   S   L   S   W   A   I   W   T       128

385   AGG GCA TGG                                                        393
129    R   A   W                                                        131
```

FIG. 4

| | | | | | | | | | | | | |
|---|---|---|---|---|---|---|---|---|---|---|---|---|
| 1<br>1 | CTG<br>L | AAT<br>N | GCC<br>A | CTC<br>L | ATG<br>M | ACT<br>T | CTT<br>L | CAG<br>Q | TGC<br>C | CCA<br>P | AAA<br>K | AGG<br>R | AAC<br>N | ATG<br>M | TTT<br>F | ACG<br>T | 48<br>16 |
| 49<br>17 | AGA<br>R | ATT<br>I | GCC<br>A | CCT<br>P | CAA<br>Q | GCA<br>A | GGG<br>G | AGA<br>R | GTG<br>V | TCA<br>S | AGA<br>R | AAG<br>K | GTG<br>V | TCC<br>S<br>NcoI | ATG<br>M | 96<br>32 |
| 97<br>33 | GCT<br>A | TCA<br>S | ACT<br>T | CTT<br>L | CAT<br>H | GCT<br>A | CCA<br>P | AGC<br>S | GTG<br>V | TTC<br>F | GAC<br>D | AAG<br>K | CTG<br>L | AAG<br>K | GCT<br>A | 144<br>48 |
| 145<br>49 | GGG<br>G | AGG<br>R | CCT<br>P | CAA<br>Q | GAT<br>D | GAA<br>E | GTG<br>V | TTG<br>L | AGA<br>R | GTG<br>V | TTC<br>F | AAC<br>N | TCT<br>S | CTG<br>L | GAG<br>E | GGT<br>G | TGG<br>W | GCC<br>A | 192<br>64 |
| 193<br>65 | AGG<br>R | GAC<br>D | AAC<br>N | ATC<br>I | CTT<br>L | GTG<br>V | CAC<br>H | CTG<br>L | TTC<br>F | AAA<br>K | TCC<br>S | GTA<br>V | TCT<br>S | CTG<br>L | GAG<br>E | AAC<br>N | TCA<br>S | CAG<br>Q | 240<br>80 |
| 241<br>81 | CCG<br>P | CAA<br>Q | GAC<br>D | TAT<br>Y | CTG<br>L | CCC<br>P | GAT<br>D | CCC<br>P | ACA<br>T | TCC<br>S | GAT<br>D | GCA<br>A | CTC<br>L | CCT<br>P | GCA<br>A | TTT<br>F | GAA<br>E | GAT<br>D | CAA<br>Q | 288<br>96 |
| 289<br>97 | GTC<br>V | AAG<br>K | GAG<br>E | ATG<br>M | AGA<br>R | GAA<br>E | CGG<br>R | GCC<br>A | AAG<br>K | ATC<br>I | ACT<br>T | GAA<br>E | GAG<br>E | GCA<br>A | CTC<br>L | CCA<br>P | ACT<br>T | TAC<br>Y | TTT<br>F | 336<br>112 |
| 337<br>113 | GTT<br>V | GTT<br>V | CTT<br>L | GGA<br>G | GAC<br>D | AAC<br>N | AGA<br>R | GAC<br>D | ATG<br>M | ATC<br>I | CCT<br>P | GAT<br>D | GCA<br>A | CTC<br>L | GAC<br>D | ACT<br>T | GCT<br>A | GAG<br>E | 384<br>128 |
| 385<br>129 | ATG<br>M | TCT<br>S<br>NcoI | ACT<br>T | ATG<br>M | CTT<br>L | GCC<br>A | ACT<br>T | TGG<br>W | ATG<br>M | GAT<br>D | GGC<br>G | ATT<br>I | AAG<br>K | AGG<br>R | GAT<br>D | TGG<br>W | ACC<br>T | GCT<br>A | GAG<br>E | 432<br>144 |
| 433<br>145 | CAA<br>Q | CCT<br>P | CAT<br>H | GGC<br>G | GAT<br>D | CTT<br>L | CTC<br>L | AAC<br>N | CTC<br>L | CTC<br>L | AAG<br>K | TAT<br>Y | CTT<br>L | TAT<br>Y | GCT<br>A | GAG<br>E | GAG<br>E | 480<br>160 |
| 481<br>161 | AAC<br>N | CGC<br>R | CAT<br>H | GGC<br>G | GAT<br>D | CTT<br>L | CTC<br>L | AAC<br>N | CTC<br>L | CTC<br>L | AAG<br>K | TAT<br>Y | CTT<br>L | TAT<br>Y | GCT<br>A | GAG<br>E | GAG<br>E | 528<br>176 |
| 529<br>177 | GTT<br>V | GAT<br>D | ATG<br>M | AGG<br>R | ATG<br>M | ATT<br>I | GAG<br>E | AAG<br>K | ACT<br>T | ATT<br>I | CAA<br>Q | T | | | | | | | | 562<br>187 |

FIG. 5

```
CASTOR   ASTLKSGSKEVENLKKPFMPPREVHVQVTHSMPPQKIEIFKSLDNWAEENILVHLKPVEKCWQPQDFLP
TYPE I   ASTLGIPPLEVENKKKPFTPPREVHVQVTHSMPPEKIEIFKSLHKWAEQDLVHLKPVEKCWQPNDFLP
TYPE II  ASTLHASPLVFDKLKAGR..........PEVDELFNSLEGWARDNILLHLKSVENSWQPQDYLP
```

FIG. 6A

```
TII  GCAAAAATGGCCATGAAACTGAATGCCCTCATGACTCTTCAGTGCCCAAAAGGAACAT
TII              M  A  M  K  L  N  A  L  M  T  L  Q  C  P  K  R  N  M
CAS              M  A  M  K  L  :  N  P  F  L  S  Q  T  Q  K  L

TII  ACTCTTCATGCTAGCCCACTGGTTCGACAAGCTGAAGGCTGGGAGGCCT........
TII   T  L  H  A  S  P  L  V  F  D  K  L  K  A  G  R  P  :  -  -
CAS   :  K  S  G  S  K  E  V  E  N  :  K  P  F  M  P  P  R

TII  CTGGAGGGGTTGGGCAAGGACAACATCCTTGTGCACCTGAAATCCGTAGAGAACTCATG
TII   L  E  G  W  A  R  D  N  I  L  V  H  L  K  S  V  E  N  S  W
CAS   :  D  N  :  E  E  :  :  :  :  :  P  :  :  K  :  :

TII  ATGAGAGAACGGGCCAAGGACATCCCTGATGAATACTTTGTTGTCTTGTTGGAGACAT
TII   M  R  E  R  A  K  D  I  P  D  E  Y  F  V  V  L  V  G  D  M
CAS   L  :  :  :  :  E  :  :  :  :  D  :  :  :  :  :  :

TII  GATGACACTGGCGCCTCAACCTACTTCTTGGGCCACTTGGACCAGGGCCTTGGACTGCTGA
TII   D  D  T  G  A  Q  P  T  S  W  A  T  W  T  R  A  W  T  A  E
CAS   :  E  :  :  :  S  :  :  :  :  I  :  :  :  :  :  :

TII  AGGATGATTGAGAAGACTATTCAATATCTTATCGGTTCTGGAATGGATACAAAACAGA
TII   R  M  I  E  K  T  I  Q  Y  L  I  G  S  G  M  D  T  K  T  E
CAS   :  Q  :  :  :  :  :  :  :  :  :  :  :  :  P  R  :
```

```
GTTACGAGAATTGCCCCTCCTCAAGCAGGGAGAGTGAGATCAAAGGTGTCCATGGCTTCA   120
 F  T  R  I  A  P  P  Q  A  G  R  V  R  S  K  V  S  M  A  S    38
 P  S  F  A  L  :  :  M  :  S  T  R  S  P  K  F  Y  :  :  :    35
..........................GAGGTGGATGAATTGTTCAACTCT             195
 :  :  :  :  :  :  :  :  :  E  V  D  E  L  F  N  S              63
 E  V  H  V  Q  V  T  H  S  M  P  P  Q  K  I  :  :  K  :  :    75
GCAGCCGCAAGACTATCTGCCCGATCCCACATCCGATGCATTGAAGATCAAGTCAAGGAG   315
 Q  P  Q  D  Y  L  P  D  P  T  S  D  A  F  E  D  Q  V  K  E   103
 :  :  :  :  :  F  :  :  :  A  :  :  G  :  D  E  :  :  R  :   115
GATCACTGAAGAGGCACTCCCAACTTACATGTCTATGCTTAACAGATGTGATGGCATTAAG   435
 I  T  E  E  A  L  P  T  Y  M  S  M  L  N  R  C  D  G  I  K   143
 :  :  :  :  :  :  :  :  :  :  Q  T  :  :  T  L  :  :  V  R   155
GGAGAACCGCCATGGGCGATCTTCTCAACAAGTATCTTTATCTCTCTGGCCGAGTTGATATG   555
 E  N  R  H  G  D  L  L  N  K  Y  L  Y  L  S  G  R  V  D  M   183
 :  :  :  :  :  :  :  :  :  :  :  :  :  :  :  :  :  :  :  :   195
GAACTGTCCCTACATGGGCTTCATTTACACATCTTTCCAGGAAAGAGCCACATTCATCTCC   675
 N  C  P  Y  M  G  F  I  Y  T  S  F  Q  E  R  A  T  F  I  S   213
 :  S  :  :  L  :  :  :  :  :  :  :  :  :  :  :  :  :  :  :   235
```

```
       TGGCAACATTGCTTCTGACGAGAAACGGCCATGCCACCCCCTACACCAAATCGTGAGAAG    695
        G  N  I  A  S  D  E  K  R  H  A  T  A  Y  T  K  I  V  E  K     253
        :  :  T  :  :  A  :  :  :  :  E  :  :  :  :  :  :  :  :  :     275

AATACAAATGCCAGCTCATGCCAATGTACGATGGCTCCGATGATATGCTTTCAAGCACTTC    915
        I  Q  M  P  A  H  A  M  Y  D  G  S  D  D  M  L  F  K  H  F     303
        :  :  S  :  :  :  :  L  :  :  :  :  N  :  :  :  :  D  :  :     315

TTTTCTGGTGGATAAAATGGAACGTTGCGAAGATGACAGGCTGTCGGGTGAAGGAGAAAG    1035
        F  L  V  D  K  M  N  V  A  K  M  T  G  L  S  G  E  G  R  K     343
        :  :  :  :  :  G  R  :  K  :  D  :  L  :  :  :  A  :  :  Q     355

AGGCAAGGAGAAGAAAGCTGTGTTGCCTGTTGCCTTTCAGCTGGATTTTCAACCGTCAGATC   1155
        G  K  E  K  K  A  V  L  P  V  A  F  S  W  I  F  N  R  Q  I     383
        :  R  A  :  E  :  P  T  -  M  P  :  :  :  :  :  D  :  :  V     394

CTTTTGATGTTATTATGTTTATGCTATCGGTCGTTTGTTGTCAGATCTGGTT             1275
                                                                       385
                                                                       396
                                                                       1309
```

< 39 kDa
< 36 kDa

5,430,134

METHOD FOR PRODUCTION OF PETROSELINIC ACID AND OMEGA12 HEXADECANOIC ACID IN TRANSGENIC PLANTS

GOVERNMENT RIGHTS

The invention described herein was made in the course of work under grants from the USDA/DOE/NSF Plant Science Centers Program (#88-37271-3964), grant #FG02-90ER20021 from the U.S. Department of Energy, grant #DCB-8916311 from the National Science Foundation and the United States Government has certain rights in this invention.

FIELD OF THE INVENTION

This invention concerns the identification, introduction and expression of certain genetic informational material (i.e., DNA), which includes genes coding for proteinaceous materials and/or genes regulating or otherwise influencing the production thereof, into cells of higher plants and the regeneration of fertile plants from the genetically transformed cells. The purpose of this genetic intervention is to transfer to certain species of higher plants, from other species of plants, the genetic information which confers the ability to synthesize the fatty acid petroselinic acid. The specific example shown here is the production of petroselinic acid in tobacco, a species which does not normally accumulate this fatty acid.

BACKGROUND OF THE INVENTION

Petroselinic acid ($18:1^{\omega 12}$) is an unusual fatty acid that is found primarily in seeds of Umbelliferae (Apiaceae), Araliaceae, and Garryaceae species (Kleiman, R. & Spencer, G. F. (1982) J. Am. Oil Chem. Soc. 59, 29–38). This fatty acid is also found in Nigella sativan, a member of the family Ranunculaceae and Aucuba japonica, a member of the Cornaceae family. This fatty acid may comprise more than 80% of the total fatty acid of seeds but is virtually absent in leaves and other tissues of these plants (Ellenbracht, F., Barz, W. & Mangold, H. K. (1980) Planta 150, 114–119; Dutta, P. C. & Appelqvist, L. A. (1991) Plant Sci. 75, 177–183).

The structure of petroselinic acid differs from that of oleic acid ($18:1^{\omega 9 cis}$), a common plant fatty acid, by the position of its double bond. Because of the presence of unsaturation at the $\omega 12$ carbon atom, petroselinic acid is of potential industrial significance. Through chemical cleavage at its double bond, petroselinic acid can be used as a precursor of lauric acid (12:0), which is a component of detergents and surfactants, and adipic acid (6:0 dicarboxylic), which is the monomeric precursor of nylon 6,6. Petroselenic acid when esterified to triacylglycerols is also resistant to hydrolysis by pancreatic lipase. Therefore, such oils may have value as low calorie fats. Because this fatty acid has not previously been available in bulk quantities, not all of the potential industrial or food uses are known at present. Therefore, it may be advantageous to develop, by genetic engineering, lines of higher plants which accumulate petroselinic acid.

The pathway for petroselinic acid biosynthesis has not been previously determined. Preliminary results from a variety of [$^{14}C$]-labelling studies suggest that this fatty acid is the product of an acyl-acyl carrier protein (acyl-ACP) desaturase (FIG. 1; Cahoon, E. B. & Ohlrogge, J. B. (1991) INFORM 2, 342; unpublished data). The only acyl-ACP desaturase to have been previously characterized in plants is the $\omega 9$ stearoyl-ACP (18:0-ACP) desaturase (EC 1.14.99.6) which catalyzes the conversion of 18:0-ACP to $18:1^{\omega 9}$-ACP (Nagai, J. & Bloch, K. (1968) J. Biol. Chem. 243, 4626–4633; Jaworski, J. G. & Stumpf, P. K. (1974) Arch. Biochem. Biophys. 162, 158–165; McKeon, T. A. & Stumpf, P. K. (1982) J. Biol. Chem. 257:12141–12147). This reaction is readily assayable in tissue extracts of most plants using [$^{14}C$]18:0-ACP and cofactors including ferredoxin, NADPH, and ferredoxin-NADPH reductase (Jaworski, J. G. & Stumpf, P. K. (1974) Arch. Biochem. Biophys. 162, 158–165; McKeon, T. A. & Stumpf, P. K. (1981) Methods Enzymol. 71, 275–281). By analogy, it is thought that petroselinic acid is synthesized by $\omega 12$ desaturation of stearoyl-ACP or by $\omega 12$ desaturation of palmitoyl-ACP with subsequent two carbon atom elongation (FIG. 1). However, the in vitro synthesis of petroselinic acid from [$^{14}C$]acyl-ACPs, including [$^{14}C$]18:0-ACP, has not been detected using seed extracts of the Umbelliferae species coriander and carrot (unpublished data). Lack of such an assay complicates any attempt to characterize the biosynthetic pathway or to purify the acyl-ACP desaturase postulated to be involved in petroselinic acid synthesis.

BRIEF DESCRIPTION OF FIGURES AND TABLES

FIG. 1 shows a schematic depiction of potential enzymatic steps involved in the synthesis of petroselinoyl-ACP from stearoyl-ACP or palmitoyl-ACP.

FIG. 2A shows western blot analyses of seed extracts of Cruciferae and Umbelliferae spp. FIG. 2B shows leaf, root, and seed extracts of coriander (Coriandrum sativum L.) (B). Blot (A) lanes are: A, castor recombinant $\omega 9$18:0-ACP desaturase (Ds) (600 ng); Shanklin and Somerville, Proc. Nat'l Acad. Sci. USA 88:2510–14 (1991); B, crambe (Crambe abyssinica); C, coriander; D, wild carrot (Daucus carota L.); E, sweet cicely (Myrrhis odorata L.); and F, angelica (Angelica archangelica L.) seed extracts (50–60 µg). (Lane B is a Cruciferae species. Lanes C-F are Umbelliferae species). Blot (B) lanes are: leaf (110 µg), root (110 µg), and seed (60 µg) extracts of coriander.

FIG. 3 shows a partial cDNA sequence of a type I desaturase cDNA clone, pEC100, from coriander.

FIG. 4 shows a partial cDNA sequence of a type II desaturase cDNA clone, pEC200, from coriander. A 394 bp NcoI fragment, used as a hybridization probe to screen a coriander cDNA library, extends from nucleotide 92 to 486.

FIG. 5 shows a comparison of the partial deduced amino acid sequences of type I and type II desaturase from coriander with the sequence of the $\omega 9$ stearoyl-ACP desaturase from castor. Amino acid sequences were obtained by translation of pEC100 (Type I cDNA) and pEC200 (Type II cDNA).

FIG. 6 shows a nucleotide sequence and deduced amino acid sequence of a full-length coriander Type II acyl-ACP desaturase cDNA (TII) contained in plasmid pEC201. Also shown is a comparison of the deduced amino acid sequences of castor (Ricinus communis) $\omega 9$ 18:0-ACP desaturase (Cas) and coriander Type II acyl-ACP desaturase cDNA (pEC201). Colons indicate identical amino acids. Amino acids missing with regard to either sequence are represented by dashed lines. Alignment of the nucleotide sequence of pEC201 is maintained with a dotted line.

Figure 7:
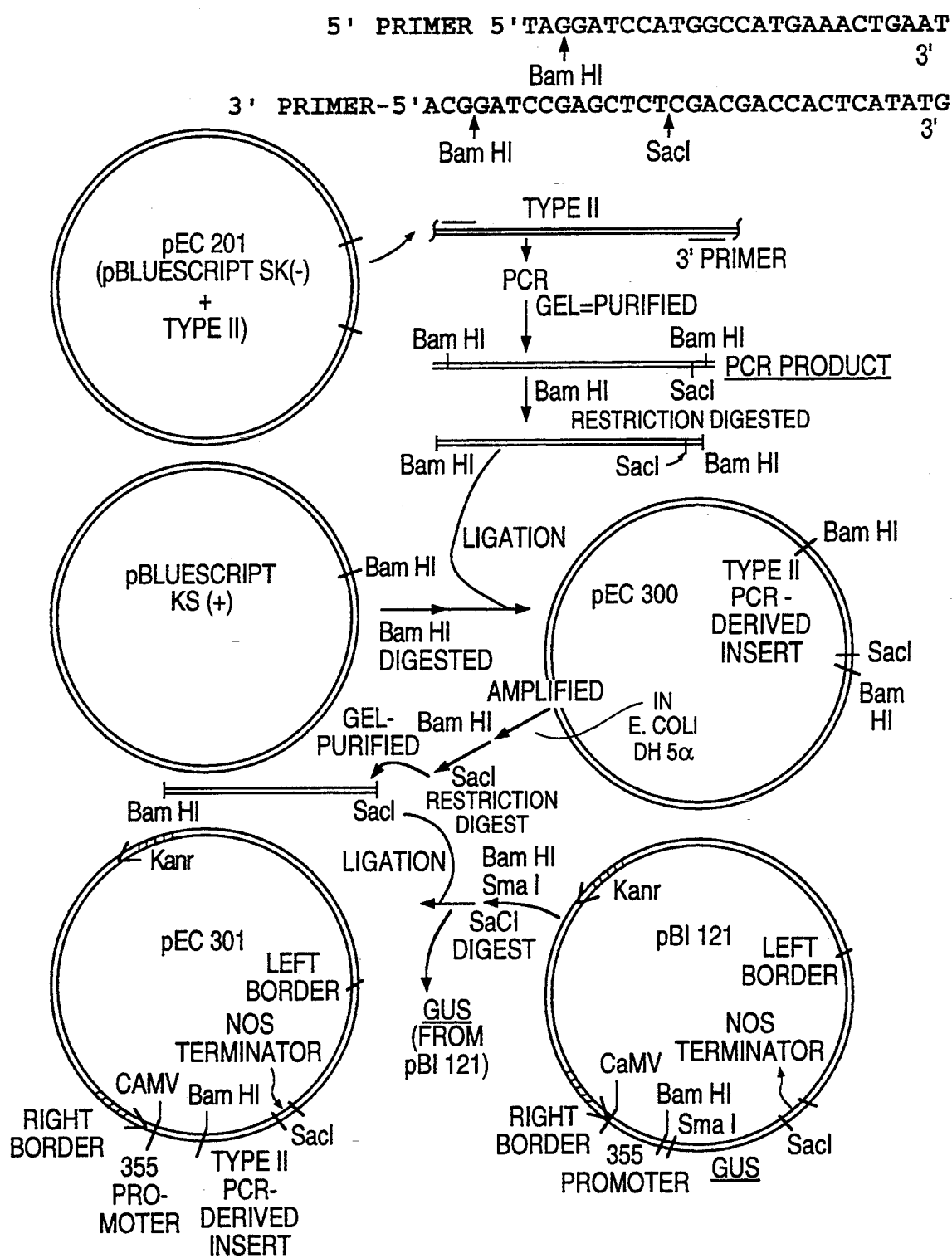

FIG. 7 shows a schematic summary of the steps involved in construction of plasmid pEC301. The purpose of this plasmid is to place the ω12 desaturase gene from coriander under transcriptional control of the CaMV 35S promoter so that it will be constitutively transcribed in higher plants.

Figure 8A:
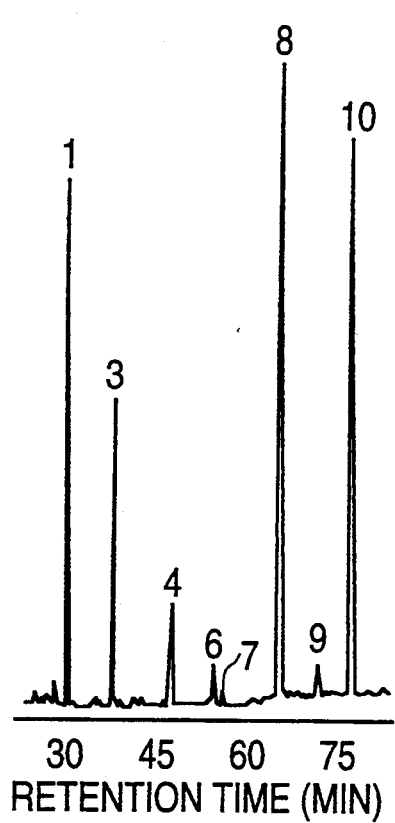
Figure 8B:
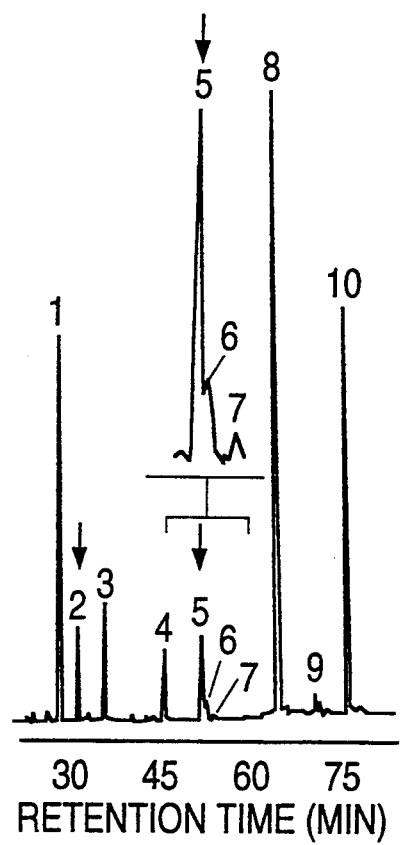

FIGS. 8A and B show the results of gas chromatography of transesterified extracts from transgenic *N. tabacum* callus tissue which resulted from transformation with pBI121 or pBI121 containing the coriander ω12 desaturase gene under transcriptional control of the CaMV 35S promoter. The arrows point to the places where petroselinic acid and cis-4-hexadecanoic acid eluted. The presence of eluting material was detected by a flame ionization detector. FIG. 8A shows gas chromatograms of extracts from callus containing pBI121; FIG. 8B shows callus line containing insert+pBI121 (pEC301). Arrows indicate fatty acids present only in callus transformed with the Type II cDNA insert. The double bond positions of 4-hexadecanoic acid ($16:1^{\omega 12}$) (Peak B) and petroselinic acid ($18:1^{\omega 12}$) (Peak E) were determined by GC-MS (see FIG. 9). Peak identification: A, 16:0; B, $16:1^{\omega 12}$; C, 17:0; D, 18:0; E, $18:1^{\omega 12}$; F, $18:1^{\omega 9}$; G, $18:1^{\omega 7}$; H, 18:2; I, 20:0; J, 18:3.

Figure 9A:
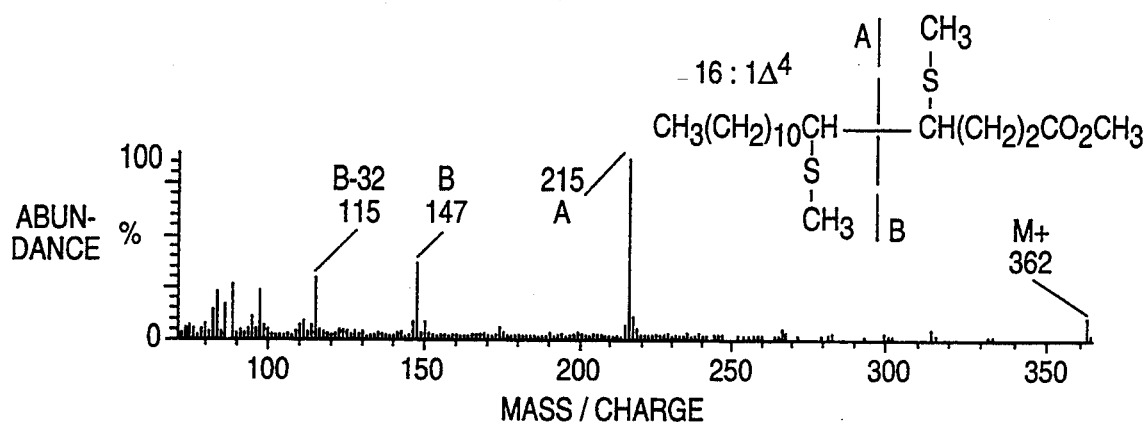
Figure 9B:
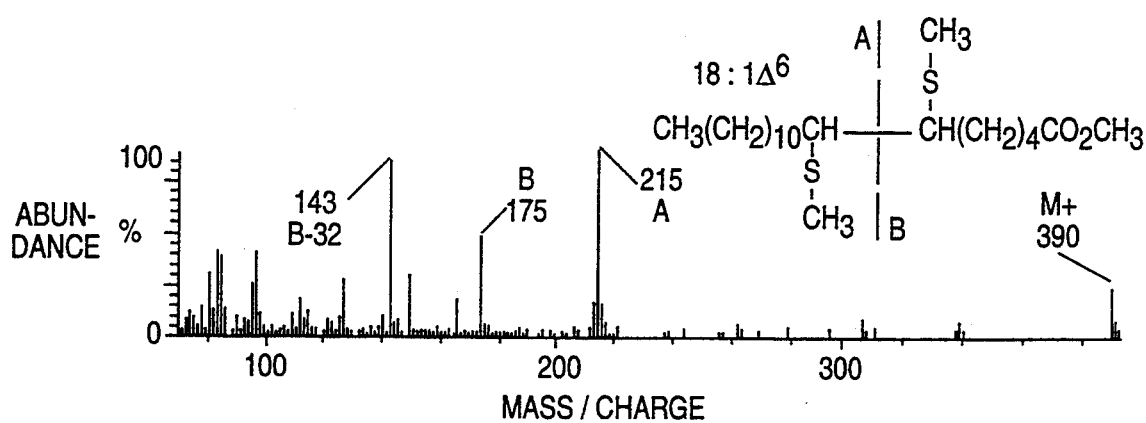

FIGS. 9A and B show the fragmentation patterns obtained by mass spectrometric analysis of dimethyl disulfide adducts of methyl 4-hexadecanoic acid ($16:1^{\omega 12}$) and petroselinic acid ($18:1^{\omega 12}$) from transgenic plants (tobacco callus) transformed with the ω12 desaturase gene. FIG. 9A shows mass spectra of $16:1^{\omega 12}$ deviations. FIG. 9B shows mass spectra of $18:1^{\omega 12}$ derivatives.

Figure 10:

FIG. 10 shows western blot analysis of protein extracts from callus of transgenic tobacco. Proteins of crude extracts were separated by 11% SDS-PAGE, transferred to nitrocellulose, and probed with polyclonal antibodies against the ω9 18:0-ACP desaturase antibody of avocado. Lanes: A, coriander seed extract; B, tobacco callus transformed with the pBI121 expression vector; C, tobacco callus transformed with pBI121 containing thee coriander Type II cDNA insert (pEC301).

Figure 11A:
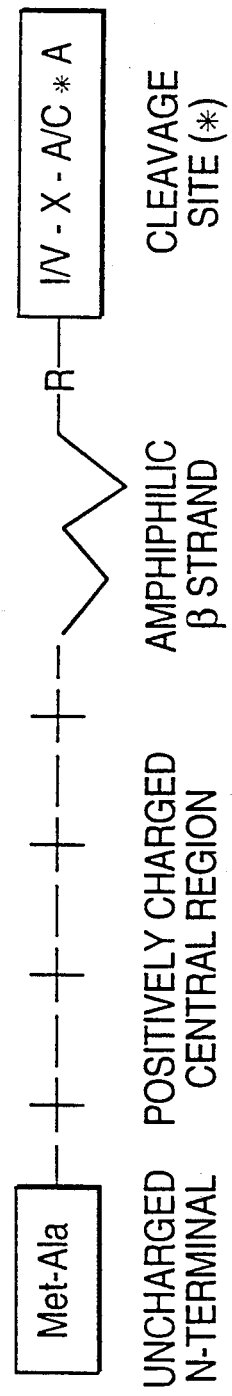
Figure 11B:
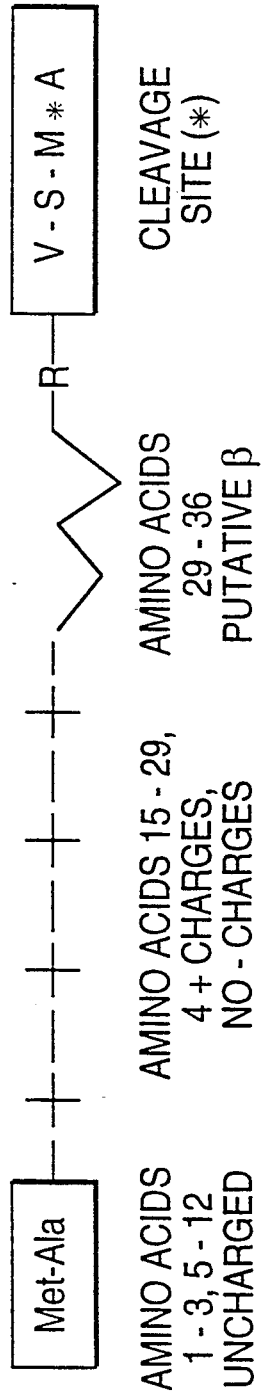

FIG. 11 shows a comparison of the amino acids sequences of a putative plastid transit peptide at the amino-terminal region of the ω12 desaturase from coriander with a consensus sequence for plastid transit peptides (Gavel, Y & von Heijne, G. (1990) FEBS Lett. 261, 455–458).

Description of Plasmids pEC100 is a partial Type I coriander cDNA desaturase clone in the vector pBluescript SK(−) (Stratagene, Calif.).

pEC 200 is a partial Type II coriander cDNA desaturase clone in the vector pBluescript SK(−) (Stratagene, Calif.).

pEC 201 is a full-length Type II coriander cDNA desaturase clone in the vector pBluescript SK(−) (Stratagene, Calif.).

pEC 300 contains an insert derived from PCR of pEC201 and used as an intermediate in the construction of pEC 301. The PCR-derived Type II insert is contained in the BamHI restriction site of the polylinker of pBluescript KS(+).

pEC 301 consists of the insert of pEC300 following BamHI/SacI restriction contained in the corresponding restriction sites of pBI121 (Clontech, Palo Alto, Calif.) behind the cauliflower mosaic virus (CaMV) 35S promoter.

SUMMARY OF THE INVENTION

The present invention describes a method for the isolation of a gene encoding a plant fatty acid desaturase which results in the production of fatty acids with a cis unsaturation at the ω12 position of the acyl chain (henceforth designated an ω12 desaturase). The basis for the method is the discovery, described here for the first time, of a high degree of structural similarity between the ω12 desaturase and all plant ω9 desaturase enzymes for which amino acid sequence information is available. This structural similarity permits the cloning of genes for ω12 desaturases by the use of antibodies raised against an ω9 desaturase. Because the nucleotide sequences of the ω12 and ω9 desaturases are also very similar, genes for ω9 desaturases can also be used to clone genes for ω12 desaturases.

The present invention also provides a method for producing genetically modified higher plants which produce and accumulate petroselinic acid. In one embodiment, petroselinic acid-producing plants are produced by stably introducing a cDNA clone of a gene, from coriander, which encodes the enzyme ω12 desaturase into cells of a plant, that do not normally produce petroselinic acid, by Ti-plasmid mediated transformation. Because cDNA clones are not normally transcribed in plant cells, the gene is modified so that it is under transcriptional control of a DNA sequence (i.e., a "promoter") which induces transcription in plant cells. The genes are also modified by the addition of an appropriate DNA sequence to the non-coding 3'-region of the genes so that the transcripts produced in plant cells are appropriately polyadenylated.

DETAILED DESCRIPTION OF THE INVENTION

Prior to setting forth the invention, it is helpful to set forth definitions of certain terms to be used hereinafter.

ω12 desaturase refers to an enzyme which replaces a single covalent bond between carbons 12 and 13, counting from the methyl end, of a fatty acid or fatty acid ester. Similarly, a ω9 desaturase introduces a double bond between the 9 and 10 carbons, counting from the methyl end of a fatty acid. The description of a desaturase as an ω9 or an ω12 desaturase is not meant to imply anything about the mechanism of action of the desaturase enzyme.

Fatty acids are abbreviated throughout as follows: 18:0, octadecanoic acid; 16:0, hexadecanoic acid; $16:1^{\omega 12}$, cis-4-hexadecanoic acid; $18:1^{\omega 12}$, cis-6octadecenoic acid; $18:1^{\omega 9}$, cis-9-octadecenoic acid. These fatty acids may be referred to as thioesters of acyl carrier protein (ACP) or coenzyme A (CoA).

Transformation means the process for changing the genotype of a recipient organism by the stable introduction of DNA by whatever means.

A transgenic plant is a plant which contains DNA sequences which are not normally present in the species, but were introduced by transformation.

Transcription means the formation of an RNA chain in accordance with the genetic information contained in the DNA.

Translation means the process whereby the genetic information in an mRNA molecule directs the order of specific amino acids during protein synthesis.

A promoter is a DNA fragment which causes transcription of genetic material. For the purposes described herein, promoter is used to denote DNA fragments that permit transcription in plant cells. The CaMV 35S-promoter is a DNA fragment from the cauliflower mosaic virus that causes relatively high levels of transcription in many different tissues of many species of higher plants. Benfey, P. N. and Chua, N. H. Science 250:959–966 (1990).

A poly-A addition site is a nucleotide sequence which causes certain enzymes to cleave mRNA at a specific site and to add a sequence of adenylic acid residues to the 3'-end of the mRNA.

In describing the progeny of transgenic plants, it is useful to adopt a convention which designates how may generations of self-pollination have elapsed since the introduction of DNA. Herein, we designate the original transformant the T0 generation. The progeny resulting from self-pollination of this generation is designated the T1 generation and so on.

Although the experiments discussed hereinafter concern the plant species *Nicotiana tabacum* (L.), the process described is generally applicable to any higher plant for which a method of transformation is available, particularly oil seeds such as corn, soy, rape seed, canola, safflower, sunflower and cotton seed. Similarly, although the process described herein concerns the use of genes from coriander, the process described is generally applicable to the use of genes from any organism which is capable of synthesis of petroselinic acid.

EXPERIMENTAL DETAILS

Experimental Design

The invention described here arose from experiments designed to test the hypothesis that the ω12 desaturase from coriander was structurally related to ω9 18:0-ACP desaturase from avocado and other plants. Using an antibody raised against the ω9 18:0-ACP desaturase of avocado (Shanklin, J. & Somerville C. Proc. Natl. Acad. Sci. USA 88, 2510–2514 (1991)), a cDNA expression library was screened and a cDNA from coriander was isolated which encodes a polypeptide of approximately 36 kDa which is specific to tissues which synthesize petroselinic acid. Expression of this cDNA clone in tobacco confirmed that the 36 kDa protein is a fatty acid desaturase sufficient for the production of petroselinic acid in transgenic plant tissue.

The production of petroselinic acid in progeny of transformed plants requires the completion of a sequence of steps as follows: (1) Analysis of the extracts of tissues from plants which produce petroselinic acid for the presence of a protein which is structurally related to the ω9 desaturase by immunological analysis, (2) preparation of a cDNA library from developing seeds of coriander, (3) the isolation of a cDNA clone for the ω12 desaturase from coriander, and the determination of the nucleotide sequence of the cDNA clone, (4) the construction of a bacterial plasmid containing the cDNA under transcriptional control of a suitable plant promoter, (5) the transfer of this plasmid into *Agrobacterium tumefaciens*, and the use of *A. tumefaciens* to introduce the gene into cells of a plant species which do not normally produce petroselinic acid (i.e., *N. tabacum* in this example), (6) analysis of the function of the ectopic gene in the transformed plants to ensure that it is expressed and that the gene product is functional, (7) the analysis of the transgenic plant material for the presence of petroselinic acid. These steps are described in detail in the following sections.

Immunological identification of a novel desaturase in Umbelliferae.

Figure 1A:
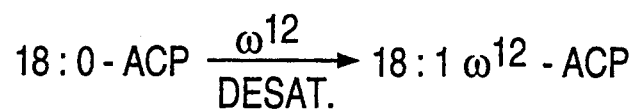
Figure 1B:
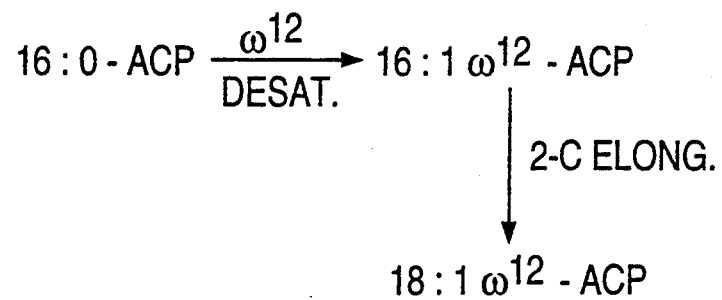
Figure 2A:
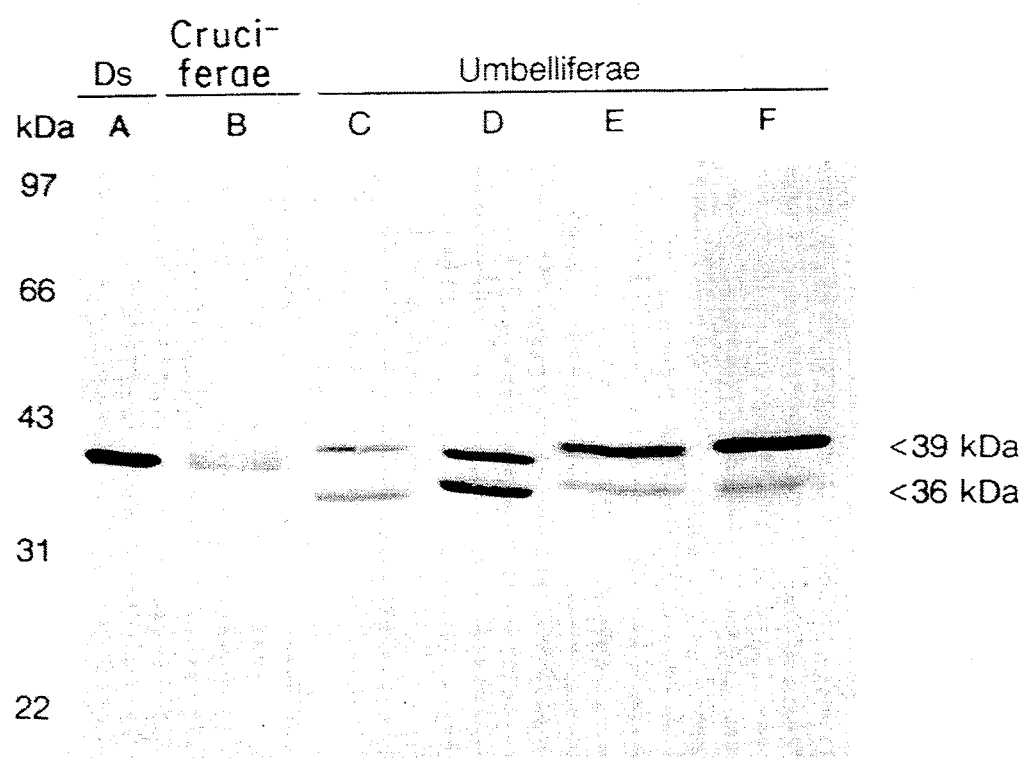
Figure 2B:
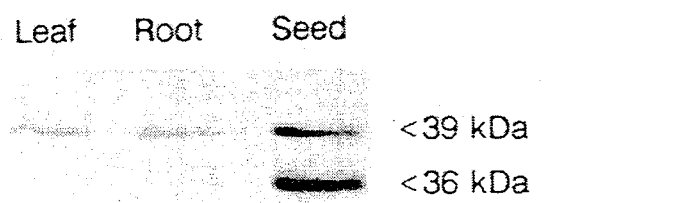

A polyclonal antibody raised against the ω9 18:0-ACP desaturase of avocado (Shanklin, J. & Somerville C. Proc. Natl. Acad. Sci. USA 88, 2510–2514 (1991)) was used to assess the antigenic relationship between this enzyme and a proposed acyl-ACP desaturase responsible for petroselinic acid synthesis in seed of Umbelliferae species. Correlative evidence was obtained by comparison of western blots of proteins extracted from tissues which synthesize petroselinic acid versus tissues which do not synthesize this fatty acid. Extracts were prepared from developing seeds of *Coriandrum sativum*, *Crambe abyssinica*, *Daucus carota*, *Myrrhis odorata*, *Angelica archangelica*, and the proteins separated by SDS-PAGE. All species which contained petroselinic acid also contained proteins of approximately 39 and 36 kDa which displayed immunological cross-reactivity with an antibody against the ω9 18:0-ACP desaturase from avocado (FIG. 2). However, tissues which do not produce petroselinic acid (e.g., seeds of non-Umbelliferae, -Araliaceae, or -Garryaceae species and vegetative tissues of Umbelliferae species) contained only a 39 kDa protein with antigenic similarity to the ω9 18:0-ACP desaturase of avocado (FIGS. 2A, B). From these results, it was hypothesized that the 39 kDa protein observed to cross-react with the anti-avocado antibody on all western blots is the ω9 18:0-ACP desaturase, an enzyme nearly ubiquitous to all higher plant tissues. Because of its appearance only in tissues which contain petroselinic acid, the 36 kDa protein was postulated to be an acyl-ACP desaturase responsible for the synthesis of this fatty acid.

Isolation of a cDNA clone for ω12 desaturase

As an initial step in determining the function of the 38 and 36 kDa proteins identified on western blots, cDNA clones encoding both of these peptides were isolated. A cDNA library was prepared from RNA extracted from developing seeds of coriander (*Coriandrum sativum*) as described in MATERIALS AND METHODS. Two hundred fifty thousand clones of the coriander cDNA library were screened with the antibody raised against the ω9 stearoyl-ACP desaturase of avocado. Fifteen clones were observed to cross-react with this antibody. Seven of these clones were purified and phagemid DNA was excised ("zapped") from each. Partial DNA nucleotide sequences were subsequently obtained for these clones using dideoxy sequencing. Two classes of cDNAs were identified from the resulting nucleotide sequence. One class (Type I) possessed a very high degree of homology with known sequences of cDNAs encoding the ω9 stearoyl-ACP desaturase. The nucleotide sequence of the second class (Type II) was more divergent and lacked a region of 45 nucleotides. It was assumed that this second class of cDNA clones (Type II) encoded the 36 kDa putative ω12 desaturase. The partial sequences of two cDNA clones, representing the two classes and designated pEC100 and pEC200 are presented in FIG. 3 and FIG. 4, respectively. cDNA clones within each of the two classes, designated Type I and Type II, contained perfect nucleotide identity in their 3' untranslated regions. In addition, analysis of the putative translation product from the 5' region of nucleotide sequence from Type I and Type II cDNA clones revealed that both classes contained considerable amino acid sequence identity with that of previously isolated ω9 18:0-ACP desaturase cDNAs of castor, cucumber, and safflower (Shanklin, J. & Somerville C. (1991) Proc. Natl. Acad. Sci. USA 88, 2510-2514; Shanklin, Mullins and Somerville, (1991) Plant Physiol. 97:467-468; Thompson, G. A., Scherer, D. E., Foxall-Van Aken, S., Kenny, J. W., Young, H. L., Shintani, D. K., Kirdl, J. C. & Knauf, V. C. (1991) Proc. Natl. Acad. Sci. USA 88, 2578-2582). However, a region within the 5' region of the putative open reading frame of Type II cDNA clones exhibited marked amino acid divergence with a similar region in translated ω9 18:0-ACP desaturase clones (FIG. 5). This divergence included the absence of 15 amino acids in the putative polypeptide product of the Type II clone relative to that of the Type I clone and the previously reported ω9 18:0-ACP desaturase cDNA clones.

The ω9 18:0-ACP desaturase is found in the plastid of plant cells (Jaworski, J. G. (1987) in The Biochemistry of Plants, Vol. 9, eds Stumpf, P. K. & Conn, E. E. (Academic Press, New York), pp. 159-173). A similar localization would be expected for other acyl-ACP desaturases. However, the longest Type I & II cDNA clones obtained through antibody screening of the expression library lacked nucleotide sequences encoding an entire plastid transit peptide. A full-length Type II cDNA clone was therefore obtained by screening 200,000 plaques of the coriander library with an [$\alpha$-$^{32}$P] dCTP random-labelled DNA probe derived from a 394 bp NcoI restriction fragment from the 5' end of the largest partial Type II clone (designated pEC200). The approximate size of clones hybridizing to this probe was determined by polymerase chain reaction (PCR) and agarose gel electrophoresis of the resulting products. Primers for the PCR amplification were pBluescript SK and KS (Stratagene) polylinker primers and a nucleotide sequence derived from the 5' end of the longest Type II clone. The sequences of the latter primer was 5'GCACTGAAGAGTCATGAG3'. One clone was identified which was approximately 25 bp longer than the previously longest Type 2 clone. Following purification, phagemid excision, and DNA nucleotide sequencing, this clone (designated pEC201) was identified as having enough DNA at the 5' end to encode a sufficiently long transit peptide-encoding sequence. This putative full-length clone was completely sequenced by the chain termination method on both strands (FIG. 6). A comparison of the deduced amino acid sequence with that of the castor sequence is shown in FIG. 6. This cDNA contained a consensus translational start at nucleotide 7 and an open-reading frame of 1155 nucleotides encoding a 385-amino acid peptide. By homology with the published nucleotide sequences of the castor ω9 18:0-ACP desaturase cDNA clone (Shanklin, J. & Somerville C. Proc. Natl. Acad. Sci. USA 88, 2510-2514 (1991)), the encoding sequence of the mature protein likely begins at nucleotide 115. The first 108 bp of the open reading frame, therefore, are thought to encode a plastid transit peptide of 36 amino acids which is 3 amino acids longer than those of the ω9 18:0-ACP desaturase cDNA clones reported to date (Shanklin, J. & Somerville C. Proc. Natl. Acad. Sci. USA 88, 2510-2514 (1991); Thompson, G. A., Scherer, D. E., Foxall-Van Aken, S., Kenny, J. W., Young, H. L., Shintani, D. K., Kirdl, J. C. & Knauf, V. C. Proc. Natl. Acad. Sci. USA 88, 2578-2582 (1991)).

Expression of the Coriander ω12 desaturase cDNA in Transgenic Tobacco.

The identity of the Type II cDNA as a ω12 desaturase was confirmed by expressing the cDNA clone in transgenic tobacco, a plant which normally does not contain detectable levels of petroselinic acid.

In order to obtain transcription of a cDNA clone in higher plants, the cDNA clone must be modified by the addition of a plant promoter so that it is transcribed when introduced into higher plants. In addition, it is common practice to add a poly-A addition site to the 3' region of the cDNA clone in order to obtain proper expression of the genes in higher plants. Both of these requirements were satisfied by cloning the cDNA clone for the ω12 desaturase cDNA clone from pEC201 into the binary Ti plasmid vector pBI121 (Clontech, Palo, Alto, Calif.).

PCR primers were designed from the final 18 nucleotides of the 5' and 3' ends, respectively, of pEC201. The primers were designed to encode restriction enzyme cleavage sites on the flanking ends of these primers. The 5' PCR primer was designed to contain a BamHI restriction site, and the 3' PCR primer was designed to contain a SacI site flanked by a BamHI restriction site. The nucleotide sequences of the 5' and 3' PCR primers were 5'TAGGATCCATGGCCATGAAACTGAAT3' and 5'ACGGATCCGAGCTCTCGACGACCACTCATATG3', respectively Using these primers, clone pEC201 was amplified by PCR using Vent DNA polymerase (New England Biolabs). The product was gel-purified and restriction digested with BamHI. The resulting DNA was cloned into the BamHI restriction site of pBluescript KS(+) (resulting plasmid pEC300) and amplified in E. coli strain DH5α cells. This cloned DNA was subsequently restriction digested with BamHI and SacI. Following gel purification, this restriction fragment containing the full-length sequence of pEC201 was cloned into the BamHI/SacI cloning sites of the plant expression vector pBI121 (Clontech, Palo Alto, Calif.) behind the CaMV 35S promoter. The resulting plasmid (designated pEC301) was found to have the ω12 desaturase gene in the correct orientation, relative to the CaMV 35S promoter and poly-A addition site of pBI121, so that it would be expected to be expressed in higher plants. A schematic summary of the steps involved in construction of pEC301 is presented as FIG. 7.

The plasmid pEC301 was introduced into Agrobacterium tumefaciens strain LBA4404 by electroporation (Mersereau, M., Pazour, G. J. & Das, A. (1990) Gene 90, 149-151). As a control, pBI121 lacking an insert was also introduced into Agrobacterium by electroporation. The transformed Agrobacterium was grown at 27° C. in the presence of 25 μg/ml of kanamycin to maintain selection for the presence of the plasmid. Tobacco leaf disks were inoculated with the resulting Agrobacterium cells carrying pBI121-derived plasmids and placed on shoot induction medium containing naphthalene acetic acid and benzylaminopurine (Rogers, S. G., Horsch, R. B. & Fraley, R. T. (1986) Methods Enzymol. 118:627-648). This resulted in the recovery of kanamycin resistant transgenic callus tissues in each case which gave rise to fertile shoots which produced seeds. Each plant which produced seeds was assigned a different number to indicate that it represented a distinct transformation event. A total of 20 transgenic plants were recovered from tissue treated with A. tumefaciens carrying the plasmid pEC301. These were designated COR-TII 1, 2, 3, ... 20.

Analysis of the Fatty Acid Composition of the Transgenic Tobacco Tissue

The fatty acid composition of the cellular lipids in the resulting transgenic tobacco callus was examined by gas chromatography (FIG. 8). Callus transformed with the Type II cDNA contained two fatty acids not present in callus transformed with only the pBI121 vector. The retention times of these fatty acid methyl esters coincided with that of methyl hexadecanoic acid (16:1) and methyl petroselinate (18:1$\omega$12). In all calli samples analyzed, levels of each of these fatty acids were 1 to 4% (on a weight basis) of the total. Table I summarizes the results from the fatty acid analyses of the transgenic calli. Table I. Fatty acid analysis of transgenic tobacco callus. Samples were prepared by tranesterification of callus samples in 10% boron trichloride/methanol (see MATERIALS AND METHODS). Fatty acid composition is presented as weight percent (wt %) of the total fatty acid±standard deviation (SD) (n=3 for pBI121, n=10 for pEC301)

TABLE I

| Fatty Acid | pBI121 (wt % ± SD) | pEC301 (wt % ± SD) |
| --- | --- | --- |
| 16:0 | 20.7 ± 0.5 | 18.9 ± 2.0 |
| 16:1$\omega$12 | 0 | 3.3 ± 1.2 |
| 16:1$^a$ | 0.6 ± 0.4 | 0.3 ± 0.3 |
| 18:0 | 4.3 ± 1.1 | 5.8 ± 1.1 |
| 18:1$\omega$12 | 0 | 2.7 ± 0.9 |
| 18:1$\omega$9 | 1.4 ± 0.7 | 2.1 ± 1.7 |
| 18:1$\omega$11 | 0.5 ± 0.2 | 0.4 ± 0.1 |
| 18:2 | 40.2 ± 5.6 | 40.1 ± 6.3 |
| 18:3 | 31.2 ± 3.7 | 25.3 ± 5.7 |
| 20:0 | 0.8 ± 0.1 | 1.1 ± 0.5 |

Table I shows the fatty acid composition of callus transformed with pBI121 vector or PEC301.
$^a$16:1 isomers (other than 16:1$\omega$12) detected included primarily 16:1$\omega$7 and, in some samples, small amounts of 16:1$\omega$13trans).

Table I shows the fatty acid composition of callus transformed with pBI121 vector or PEC301.

To determine the position of the double bond in the new peak of hexadecanoic acid and confirm the identity of the putative methyl petroselinate peak, monounsaturated fatty acid methyl esters of the total lipids from transgenic calli were purified by argentation TLC (Morris, L. J., Wharry, D. M. & Hammond, E. W. (1967) J. Chromatog. 31, 69–76), derivatized with dimethyl disulfide (Yamamoto, K., Shibahara, A., Nakayama, T. & Kajimoto G. (1991) Chem. Phys. Lipids 60, 39–50), and analyzed by gas chromatography-mass spectrometry (FIG. 9). The mass spectrum of the derivatized petroselinic acid contained the same diagnostic ions as a petroselinic acid standard. In addition, the mass spectrum of the derivatized hexadecanoic acid of the transgenic callus contained ions distinct for a $\omega$12 isomer (Francis, G. W. Chem. Phys. Lipids (1981) 29, 369–374).

Expression of the Type II cDNA was examined by western blot analysis of the transgenic tobacco callus using the $\omega$9 18:0-ACP desaturase antibody (FIG. 10). A protein of 36 kDa was detected in extracts of callus containing the Type II cDNA but was absent in callus transformed with only the pBI121 vector. These results therefore confirm that the 36 kDa protein observed on western blots of coriander and other Umbelliferae seed is an acyl-ACP desaturase associated with the synthesis of petroselinic acid as well as 16:1$\omega$12.

DISCUSSION

In these studies, it has been demonstrated that developing coriander seeds contain two polypeptides of approximately 36 and 39 kilodaltons which are antigenically related to an $\omega$9 desaturase from avocado. It was further demonstrated that a cDNA clone from coriander encoding the smaller of the two polypeptides had a high degree of overall nucleotide and deduced amino acid sequence identity to the $\omega$9 desaturases. It was further demonstrated that, when stably introduced into transgenic tobacco under transcriptional control of the cauliflower mosaic virus 35S promoter, this cDNA caused the accumulation of petroselinic acid and 16:1$\omega$12 in tobacco. Thus, this result demonstrates that the cDNA clone pEC201 encodes a fully functional $\omega$12 desaturase. This finding clearly demonstrates that the biosynthetic pathway of petroselinic acid involves an acyl-ACP desaturation step. Previously, oleic acid was the only plant fatty acid known to be synthesized through such a metabolic route (Nagai, J. & Bloch, K. (1968) J. Biol. Chem. 243, 4626–4633; Jaworski, J. G. & Stumpf, P. K. (1974) Arch. Biochem. Biophys. 162, 158–165).

Because it has not yet been possible to develop an assay for the $\omega$12 desaturase in any plant, the $\omega$12 desaturase activity in the transgenic plants were not determined directly. Desaturases typically introduce double bonds into plant fatty acids using either of two substrate-types (Jaworski, J. G. (1987) in The Biochemistry of Plants, Vol. 9, eds Stumpf, P. K. & Conn, E. E. (Academic Press, New York), pp. 159–173; Browse, J. & Somerville, C. (1991) Annu. Rev. Plant Physiol. Plant Mol. Biol. 42, 467–506): (1) a fatty acid bound to a glycerolipid such as phosphatidylcholine or (2) a fatty acid bound to acyl carrier protein (ACP). In preliminary experiments, [1-$^{14}$C]18:0 and [1-$^{14}$C]16:0 fed to endosperm slices of coriander (an Umbelliferae species) were incorporated into glycerolipids but not desaturated (Cahoon, E. B. & Ohlrogge, J. B. (1991) INFORM 2, 342). However, crude homogenates of coriander were capable of de novo synthesis of petroselinic acid from [2-$^{14}$C]malonyl-CoA. The resulting [$^{14}$C]petroselinic acid was detected primarily as free fatty acid and a smaller portion as an ammonium sulfate precipitate, presumably representing the acyl-ACP fraction (Cahoon, E. B. & Ohlrogge, J. B. (1991) INFORM 2, 342). These data, therefore, suggested that petroselinic acid derives from an acyl-ACP rather than a glycerolipid-type desaturase.

In the experiments described in this work, the product of the $\omega$12 desaturase gene from coriander is most likely localized in the plastid, since the polypeptide contains an amino terminal sequence with similarity to other transit peptides (FIG. 11). It is not known where the petroselinic acid accumulates within the cells of the transgenic plants.

An unexpected finding from this work is the appearance of nearly equal levels of 16:1$\omega$12 and petroselinic acid in tobacco callus expressing the 36 kDa desaturase. Several 16:1 isomers are detectable in lipid extracts of coriander seed. One of these isomers has been identified by mass spectrometry as 16:1$\omega$12. However, amounts of 16:1$\omega$12 are typically $\leq$ 1 wt % of the total fatty acid of coriander seed extracts. In contrast, petroselinic acid accounts for $\geq$ 70 wt % of the fatty acid of coriander seed. Thus, petroselinic acid-accumulating species, such as coriander, may contain additional enzymes, not present in other species such as tobacco, which regulate directly or indirectly the relative activity of the 12 desaturase on 16:0-ACP versus 18:0-ACP.

Because of the occurrence of both petroselinic acid and 16:1$\omega$12 in transgenic tobacco, the direct precursor of petroselinic acid cannot be definitively identified. One possibility is that petroselinic acid results from the 2-carbon elongation of 16:1$\omega$12-ACP, analogous to the synthesis of cis -vaccenoyl-ACP ($\omega$7 18:1-ACP) from palmitoleoyl-ACP ($\omega$7 16:1-ACP) in E. coli (Scheubert, G. & Bloch, K. (1962) J. Biol. Chem. 237, 2064–2068). Alternatively, petroselinic acid may be synthesized directly from 18:0-ACP. If the latter case is true, the 36 kDa enzyme would be expected to recognize the $\omega$12 carbon of both 16:0- and 18:0-ACP as the site of desaturation. This protein would therefore lack strict specificity for the carbon chain length of its acyl-ACP substrate.

The synthesis of petroselinic acid and 16:1$\omega$12 in transgenic tobacco is to our knowledge is the first demonstration of the production of new unsaturated fatty acids via gene transfer technology. This finding may allow for the development of a new plant oil, i.e. a high petroselinate oil, in an existing oilseed crops such as rapeseed, sunflower, soybean, cotton, safflower or oil palm. However, levels of petroselinic acid in the transgenic tobacco callus were only 1 to 4 wt % of the total fatty acid. This rather low amount of petroselinic acid may suggest that other factors are required for high levels of synthesis. Such factors may include, for example, an acyl-ACP thioesterase specific for $\omega$12 18:1-ACP. It is also possible that petroselinic acid may not be a preferred substrate for membrane lipid metabolism. Thus, the relatively low levels of accumulation in callus tissues may reflect rapid degradation of the fatty acid when it is utilized for membrane lipids. As such, higher levels of this fatty acid might be expected in the seed oil of transgenic plants.

MATERIALS AND METHODS

General methods

E. coli strains harboring plasmids were grown in LB broth supplemented with kanamycin (50 $\mu$g/ml) or ampicillin (50 $\mu$/ml). Large-scale preparations of plasmid DNA was done by the alkaline lysis and polyethylene glycol precipitation procedure as described by Sambrook J., Fritsch E. F. and Maniatis, T., Molecular Cloning, A Laboratory Manual, Cold Spring Harbor Laboratory Press (1989). Plasmid DNA was cleaved with restriction endonucleases according to the manufacturers recommendations (New England Biolabs, Beverly, Mass; Boehringer Mannheim Biochemicals, Indianapolis, IN; Stratagene, LaJolla, Calif.), separated by agarose gel electrophoresis and visualized by ethidium bromide staining as described by Sambrook J., Fritsch E. F. and Maniatis, T., Molecular Cloning, A Laboratory Manual, Cold Spring Harbor Laboratory Press (1989). The DNA fragments were recovered from agarose gels using "GENE CLEAN" II (Bio101, LaJolla, Calif.) according to the manufacturer's protocol. In some experiments, the recessed 3' termini of DNA fragments were converted into blunt ends with T4 DNA polymerase using the protocol described in Sambrook J., Fritsch E. F. and Maniatis, T., Molecular Cloning, A Laboratory Manual, Cold Spring Harbor Laboratory Press (1989). Ligation of DNA fragments with cohesive or blunt ends was done at 14° C. for 4 to 16 h in buffer containing 50 mM Tris-HCl (pH 7.6), 5 mM MgCl$_2$, 5% (w/v) polyethylene glycol 8000, 0.5 mM ATP and 5 mM dithiothreitol as described by Sambrook J., Fritsch E. F. and Maniatis, T., Molecular cloning, A Laboratory Manual, Cold Spring Harbor Laboratory Press (1989). A fraction of the ligation reaction was transferred into E. coli by the rubidium chloride method as described by Hanahan, D., J. Mol. Biol. 166:557–580 (1983). The transformed bacteria were plated on agar plates containing LB broth and either 50 $\mu$g/ml kanamycin or 50 $\mu$g/ml ampicillin. Bacterial colonies containing recombinant plasmids were identified by either blue/white selection or by restriction digestion patterns of purified plasmid DNA as described by Sambrook J., Fritsch E. F. and Maniatis, T., Molecular Cloning, A Laboratory Manual, Cold Spring Harbor Laboratory Press (1989). Preparation of radiolabeled DNA probes and hybridization are described in a following section. Small-scale preparation of plasmid DNA was done by the alkaline lysis method as described by Sambrook J., Fritsch E. F. and Maniatis, T., Molecular cloning, A Laboratory Manual, Cold Spring Harbor Laboratory Press (1989) .

Polymerase chain reaction (PCR) was performed using a Perkin-Elmer Cetus DNA thermal cycler (Perkin-Elmer, Norwalk, Conn.). A typical reaction mixture contained 50–100 ng of template, 0.25 $\mu$M of 5' and 3' primers, 0.16 mM dNTPs, 1$\times$ reaction buffer, and 1 U Taq DNA polymerase (Boehringer Mannheim) in 25 $\mu$l Reactions were performed with a Perkin-Elmer/Cetus thermal cycler with a program of 5 min at 94° C.; 30 cycles of 1.1 min at 94° C., 2 min at 55° C, 3 min at 72° C.; followed by 10 min at 72° C. PCR products were purified with Geneclean II (Bio101) according to the manufacturer's protocol.

Preparation of a cDNA library from coriander.

Coriander (Coriandrum sativum L.) plants were grown under in a glasshouse at Michigan State University with at least 10 h of daily illumination provided by natural or supplemental lighting. Total RNA was isolated from the endosperm and embryo of developing coriander seeds using a procedure modified from that described by Hall, T. C., Ma, Y., Buchbinder, B. U., Pyne, J. W., Sun, S.M. & Bliss, F. A. (1978) Proc. Natl. Acad. Sci. USA 75, 3196–3200. Endosperm containing an embedded embryo was collected from coriander cremocarps (fruits) at stages ranging from early through mid-development and ground to a powder in liquid nitrogen. Samples were transferred to a glass (Elvehjem) homogenizer containing a buffer (3.5 ml/g tissue) preheated to 80° consisting of 0.2M sodium borate, 30 mM EGTA, 1% SDS, 1% deoxycholate, 2% polyvinylpyrollidone 40,000, and 10 mM DTT (dithiothreitol) (freshly added) (final pH 8.5). Tissue was homogenized for an additional 2 min. The homogenate was transferred to a sterile tube and incubated with Proteinase K (Boehringer Mannheim, Indianapolis, Ind.) (0.5 mg/ml) at 42° C. for 1.5 h with shaking. To the homogenate, KCl was added to a final concentration of 0.16M. Following 1 h incubation on ice, the sample was centrifuged at 12,000$\times$g at 4° C. for 20 min. The recovered supernatant was adjusted to 2M LiCl, and RNA was precipitated by overnight incubation on ice. The RNA pellet was washed three times with 5 ml of cold 2M LiCl and dissolved in 2 ml of 10 mM Tris pH 7.5. Insoluble material was removed by centrifugation, and RNA was ethanol-precipitated from the supernatant.

Poly A+ RNA isolation from coriander total RNA and subsequent cDNA library construction were performed by Stratagene, Inc., LaJolla, Calif. cDNA was synthesized using an oligo-dT primer and inserted into the EcoRI site of phage λ-ZAP II (Stratagene, LaJolla, Calif.).

Production of Transgenic Plants

The Ti plasmid vectors used to produced transgenic plants were first transferred into *Agrobacterium tumefaciens* strain LBA4404 (Clonetech, Calif.) by electroporation (Mersereau, M., Pazour, G. J., & Das, A. (1990) Gene 90,149–151). Leaf discs were excised from young leaves of tobacco (*N. tabacum*) and used for transformation as described by Rogers, S. G., Horsch, R. B. & Fraley, R. T. (Methods Enzymol. 118:627–648 (1986)). Briefly, discs were prepared from surface-sterilized leaves with a #8 cork borer and inoculated in a fresh, dense culture of Agrobacterium LBA4404 harboring either no plasmid, pBI121, or pEC301. Inoculated leaf disks were placed on sterile media containing Murashige and Skoog (MS) salts (Gibco, Gaithersburg, Md.), a vitamin B mixture, sucrose, kanamycin, carbenillicin, benzylaminopurine, and naphthalene acetic acid. Concentrations of these ingredients were the same as described by Rogers, S. G., Horsch, R. B. & Fraley, R. T. (Methods Enzymol. 118:627–648 (1986)). When shoots appeared from the callus, they were excised and placed in magenta boxes containing the same media as described above but lacking benzylaminopurine and naphthalene acetic acid. The formation of roots by the excised shoots in the presence of kanamycin was an indication that the plantlets had been successfully transformed with one of the plasmids described above. Shoots possessing roots of approximately 1 to 2 cm were removed from the media and transplanted in soil. The tops of pots containing rooted plants were covered with plastic wrap for a period of several days to one week to allow the plants to adjust to soil and altered humidity conditions. Transformed tobacco plants were grown under 24 h fluorescent light. Seeds were harvested from upon full maturation.

At each stage of the regeneration process described above, extracts of plant tissues, including callus, leaves, and seeds, were analyzed by western blotting for expression of the 36 kDa $\omega^{12}$ desaturase and by gas chromatography for the presence of petroselinic acid and cis-4-hexadecanoic acid. To demonstrate that petroselinic acid and cis-4-hexadecanoic acid could be reproducibly detected in transgenic callus of tobacco, leaf discs of rooted, transformed plants were placed on media described lacking antibiotics. The resulting callus was examined for expression of the 36 kDa desaturase and accumulation of petroselinic acid and cis-4-hexadecanoic acid.

Isolation and Characterization of cDNA Clones

The coriander cDNA library was subjected to immunological screening as described (Sambrook, J., Fritsch, E. F. & Maniatis, T. (1989) Molecular Cloning: A Laboratory Manual, Cold Spring Harbor Lab., Cold Spring Harbor, N.Y., pages 12.16 to 12.20) using a 1/500 dilution of immunoaffinity-purified polyclonal antibody against $\omega$9 stearoyl-ACP desaturase of avocado (Shanklin, J. & Somerville C. (1991) Proc. Natl. Acad. Sci. USA 88, 2510–2514). Immunodetection was achieved colorimetrically using an alkaline phosphatase-conjugated secondary antibody (goat-anti-rabbit IgG) and the phosphatase substrates nitroblue tetrazolium and 5-bromo-4-chloro-3-indoyl phosphate. Immunopositive clones were purified to homogeneity and pBluescript SK (−) phagemid excised ("zapped") as described (Short, J. M., Fernandez, J. M., Sorge, J. A. & Huse, W. D. (1988) Nucleic Acids Res. 16, 7583–7600).

In order to obtain a full-length Type II (see Results) cDNA clone, the coriander cDNA endosperm/embryo library was re-screened using an [$\alpha$-$^{33}$P]dCTP random-labelled DNA probe. The probe was derived from a 394 bp NcoI restriction fragment of a partial Type II cDNA clone. Library screening was performed as described (Sambrook, J., Fritsch, E. F. & Maniatis, T. (1989) Molecular Cloning: A Laboratory Manual, Cold Spring Harbor Laboratory, Cold Spring Harbor, N.Y.).

Western Blot Analysis

Plant tissues were homogenized in 50mM KPO$_4$ pH 7.2, 2 mM PMSF, 5mM sodium metabisulfite, and 5mM EDTA with a Polytron P10/35 (Brinkman, Westburg, N.Y.), passed through 2 layers of miracloth (Calbiochem, San Diego, Calif.), and mixed with SDS-PAGE sample buffer.

Protein extracts of transgenic tobacco calli were obtained by homogenization of tissue with an (Elvehjem) homogenizer in 2 ml of a solution of 0.7M sucrose, 0.5M Tris, 50 mM EDTA, 0.1M KCl (total adjusted to pH 9.4) containing 2% (v/v) $\beta$-mercaptoethanol and 2 mM PMSF. The homogenate was mixed thoroughly with 2 ml of phenol and centrifuged at 3000× g with a clinical centrifuge. The upper phenol phase was recovered, and proteins were precipitated with the addition of 10 ml of methanolic ammonium acetate and overnight incubation at −20° C. The protein pellet obtained following centrifugation was washed sequentially with methanolic ammonium acetate and acetone. The pellet was air-dried prior to addition of SDS-PAGE sample loading buffer.

Proteins of plant extracts were separated by SDS-PAGE using 11% (w/v) acrylamide gels (Laemmli, U.K. (1970) Nature 227, 680–685). Proteins were transferred from gels and fixed to nitrocellulose as described (Post-Beittenmiller, M. A., Schmid, K. M. & Ohlrogge, J. B. (1989) Plant Cell 1, 889–899). Western blot analyses were performed as described (Jabben, M., Shanklin, J. & Vierstra, R. D. (1989) J. Biol. Chem. 264, 4998–5005) using a polyclonal, immunoaffinity-purified antibody raised against the $\omega$9 18:0-ACP desaturase of avocado (Shanklin, J. & Somerville C. (1991) Proc. Natl. Acad. Sci. USA 88, 2510–2514).

Gas Chromatography and Mass Spectrometry Analysis

Fatty acid methyl esters were prepared from tobacco tissues by heating of tissue in 10% (w/v) BCl$_3$/CH$_3$OH (Alltech, Deerfield, Ill.) supplemented with 15% toluene (v/v) at 90° C. for 40 min. as described (Post-Beittenmiller, M. A., Schmid, K. M. & Ohlrogge, J. B. Plant Cell 1, 889–899 (1989)). Fatty acid methyl esters were analyzed by gas chromatography using a Hewlett-Packard 5890 gas chromatograph (GC) with a 50 m×0.25 mm ID CP-Sil88 column (Chrompack, Raritan, N.J.) and column head pressure of 7.5 psi He. Oven temperature was programmed from 155° C. (60 min hold) to 175° C. at 2.5° C./min. Injector and flame ionization detector temperatures were both 215° C. Samples of monounsaturated fatty acid methyl esters for GC-MS analyses were purified by argentation TLC essentially as described (Morris, L. J., Wharry, D. M. & Hammond, E. W. (1967) J. Chromatog. 31, 69–76). TLC plates were prepared by saturation of purchased silica gel K6 (Whatman, Hillsboro, OR) TLC plates in 15% (w/v) $AgNO_3/CH_3CN$. Fatty acid methyl esters were separated by a single development of argentation TLC plates in toluene at −20° C. (Morris, L. J., Wharry, D. M. & Hammond, E. W. (1967) J. Chromatog. 31, 69–76). Double bonds of monounsaturated fatty acids were converted to thiomethyl adducts by reaction with dimethyl disulfide in the presence of $I_2$ as described (Yamamoto, K., Shibahara, A., Nakayama, T. & Kajimoto G. (1991) Chem. Phys. Lipids 60, 39–50) except that derivatization was performed for two hours. Derivatized samples were analyzed by GC-mass spectrometry with a Hewlett-Packard 5890 GC coupled to a 5970A mass selective detector (MSD) using a 15 m×0.25 mm ID DB-17 column (J&W Scientific, Folsom, Calif.). The oven temperature was programmed from 185° C. to 230° C. at 10° C./min. Samples were applied by on-column injection. The MSD inlet temperature was 280° C. The ionizing potential of the MSD was 70 eV and the mass range scanned was 50 to 394 mass units.

Other Plants

Although the specific example of the invention described here involved the plant Nicotiana tabacum and a gene from coriander, the invention is of more general utility. The production of petroselinic acid in plants is not limited to Nicotiana tabacum, or linked to the use of the gene from coriander. A general method is described for the isolation of a $\omega 12$ desaturase from other species of higher plants by using the $\omega 12$ desaturase gene from coriander as a nucleic acid hybridization probe or by using an antibody directed against either the $\omega 12$ desaturase or a structurally related desaturase such as the $\omega 9$ desaturase used here, or by using a gene for an $\omega 9$ desaturase as a heterologous probe, or by using an $\omega 12$ desaturase nucleotide probe obtained by methods such as polymerase chain reaction using synthetic oligonucleotides designed from the coriander $\omega 12$ desaturase gene or deduced amino acid sequence and DNA from species other than coriander known to possess an $\omega 12$ desaturase and/or petroselinic acid. Although we did not describe the use of an $\omega 9$ desaturase gene as a hybridization probe, the high degree of nucleotide sequence homology between the $\omega 12$ desaturase described here and the known sequences of $\omega 9$ desaturases indicates that it would be easily accomplished by one skilled in the art. Similarly, a general method for the production of petroselinic acid in plants through the introduction of foreign DNA material encoding any $\omega 12$ desaturase into plant cells. Such plants include sunflower, soybean, rapeseed, cotton, safflower, oil palm or other plants which accumulate storage oils.

The seeds from a transgenic line which produces petroselinic acid are available from and will be maintained at Michigan state University, East Lansing, Mich. The nucleotide sequence of the gene is shown in Sequence ID NO: 1.

The mature peptides encoded by genes corresponding to the $\omega 9$ and $\omega 12$ acyl-ACP desaturases share a high degree of amino acid sequence identity (approx. 70%). Based upon information obtained from the comparison of their deduced amino acid sequences, it may be possible to interconvert these genes such that the activity of the $\omega 9$ acyl-ACP desaturase is altered to that of the $\omega 12$ desaturase or vice versa. Such genetic manipulations could be readily performed using standard laboratory practices such as polymerase chain reaction (PCR) with synthetic oligonucleotides designed from the deduced amino acid sequence of the $\omega 12$ acyl-ACP desaturase provided in this application. It is also possible that the amino acid and corresponding nucleotide sequence of the $\omega 12$ acyl-ACP desaturase may be used to engineer a wide range of acyl-ACP desaturases that have the ability to catalyze the insertion of double bonds at a variety of positions in the carbon chain of fatty acids.

The foregoing specific description is only illustrative of the present invention and it is intended that the present invention be limited only be the hereinafter appended claims.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1309 Base Pairs
        ( B ) TYPE: Nucleic Acid
        ( C ) STRANDEDNESS: Double
        ( D ) TOPOLOGY: Linear ( i i ) MOLECULE TYPE:
        ( A ) DESCRIPTION: cDNA ( i i i ) HYPOTHETICAL: No ( i v ) ANTI-SENSE: No ( v i ) ORIGINAL SOURCE:
        ( A ) ORGANISM: Coriandrum sativum ( v i i ) IMMEDIATE SOURCE:
        ( A ) LIBRARY: cDNA ( x i ) SEQUENCE DESCRIPTION: SEQ ID NO: 1:

-continued

```
GCAAAAATGG CCATGAAACT GAATGCCCTC ATGACTCTTC AGTGCCCAAA  50
AAGGAACATG TTTACGAGAA TTGCCCCTCC TCAAGCAGGG AGAGTGAGAT  100
CAAAGGTGTC CATGGCTTCA ACTCTTCATG CTAGCCCACT GGTGTTCGAC  150
AAGCTGAAGG CTGGGAGGCC TGAGGTGGAT GAATTGTTCA ACTCTCTGGA  200
GGGTTGGGCC AGGACAACA TCCTTGTGCA CCTGAAATCC GTAGAGAACT  250
CATGGCAGCC GCAAGACTAT CTGCCCGATC CCACATCCGA TGCATTTGAA  300
GATCAAGTCA AGGAGATGAG AGAACGGGCC AAGGACATCC CTGATGAATA  350
CTTTGTTGTT CTTGTTGGAG ACATGATCAC TGAAGAGGCA CTCCCAACTT  400
ACATGTCTAT GCTTAACAGA TGTGATGGCA TTAAGGATGA CACTGGCGCT  450
CAACCTACTT CTTGGGCCAC TTGGACCAGG GCTTGGACTG CTGAGGAGAA  500
CCGCCATGGC GATCTTCTCA ACAAGTATCT TTATCTCTCT GGCCGAGTTG  550
ATATGAGGAT GATTGAGAAG ACTATTCAAT ATCTTATCGG CTCTGGAATG  600
GATACAAAAA CAGAGAACTG TCCCTACATG GGCTTCATCT ACACATCTTT  650
CCAGGAAAGA GCCACATTCA TCTCCCATGC CAACACAGCC AAACTTGCTC  700
AACACTACGG TGACAAGAAC CTAGCTCAAG TGTGTGGCAA CATTGCTTCT  750
GACGAGAAAC GCCATGCCAC CGCCTACACC AAAATCGTGG AGAAGCTTGC  800
GGAGATTGAC CCAGACACCA CTGTTATCGC ATTTCTGAC ATGATGAGGA  850
AGAAAATACA AATGCCAGCT CATGCAATGT ACGATGGCTC CGATGATATG  900
CTTTTCAAGC ACTTCACAGC CGTTGCTCAG CAGATTGGAG TCTACTCTGC  950
ATGGGATTAC TGTGACATAA TTGATTTTCT GGTGGATAAA TGGAACGTTG  1000
CGAAGATGAC AGGGCTGTCG GGTGAAGGGA GAAAGGCTCA AGAATATGTT  1050
TGTAGCTTGG CTGCTAAGAT CAGGAGAGTT GAGGAGAAGG TTCAAGGCAA  1100
GGAGAAGAAA GCTGTGTTGC CTGTGGCTTT CAGCTGGATT TTCAACCGTC  1150
AGATCATCAT ATGAGTGGTC GTCGACATTC AATATTAGAC TTTTCAATTA  1200
TGCTTATGCT TTTCCTTTTG ATGTTATTAT GTTTATGCTT ATGCTATCGG  1250
TCGGTGTTTG TTGTCAGATC TGGTTATGTA AAACTTATAT TTAAATGAAT  1300
GTTGGATTT                                               1309
```

We claim:
1. An isolated DNA, wherein said DNA encodes a coriander ω12 desaturase.
2. An isolated DNA according to claim 1, wherein said DNA is as shown in SEQ ID NO: 1.
3. An isolated ω12 desaturase, wherein said desaturase is a coriander desaturase.
4. An isolated ω12 desaturase according to claim 3, wherein said desaturase has the following amino acid sequence:

MAMKLNALMTLQCPKRNMFTRIAPPQAGRVRSKVSMASTLHASPLVFDKLKA
GRPEVDELFNSLEGWARDNILVHLKSVENSWQPQDYLPDPTSDAFEDQVKEM
RERAKDIPDEYFVVLVGDMITEEALPTYMSMLNRCDGIKDDTGAQPTSWATW
TRAWTAEENRHGDLLNKYLYLSGRVDMRMIEKTIQYLIGSGMDTKTENCPYM
GFIYTSFQERATFISHANTAKLAQHYGDKNLAQVCGNIASDEKRHATAYTKI
VEKLAEIDPDTTVIAFSDMMRKKIQMPAHAMYDGSDDMLFKHFTAVAQQIGV
YSAWDYCDIIDFLVDKWNVAKMTGLSGEGRKAQEYVCSLAAKIRRVEEKVQG
KEKKAVLPVAFSWIFNRQIII.

5. An isolated DNA according to claim 1, wherein said DNA encodes a desaturase having the following amino acid sequence:

MAMKLNALMTLQCPKRNMFTRIAPPQAGRVRSKVSMASTLHASPLVFDKLKA
GRPEVDELFNSLEGWARDNILVHLKSVENSWQPQDYLPDPTSDAFEDQVKEM
RERAKDIPDEYFVVLVGDMITEEALPTYMSMLNRCDGIKDDTGAQPTSWATW
TRAWTAEENRHGDLLNKYLYLSGRVDMRMIEKTIQYLIGSGMDTKTENCPYM
GFIYTSFQERATFISHANTAKLAQHYGDKNLAQVCGNIASDEKRHATAYTKI

-continued

VEKLAEIDPDTTVIAFSDMMRKKIQMPAHAMYDGSDDMLFKHFTAVAQQIGV
YSAWDYCDIIDFLVDKWNVAKMTGLSGEGRKAQEYVCSLAAKIRRVEEKVQG
KEKKAVLPVAFSWIFNRQIII.

* * * * *